US007041083B2

(12) United States Patent
Chu et al.

(10) Patent No.: US 7,041,083 B2
(45) Date of Patent: *May 9, 2006

(54) MEDICAL CATHETER ASSEMBLY INCLUDING A REMOVABLE INNER SLEEVE AND METHOD OF USING THE SAME

(75) Inventors: Michael S. H. Chu, Brookline, MA (US); Laddvanh Bouphavichith, Clinton, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 380 days.

This patent is subject to a terminal disclaimer.

(21) Appl. No.: 10/083,428

(22) Filed: Feb. 26, 2002

(65) Prior Publication Data

US 2003/0163119 A1    Aug. 28, 2003

(51) Int. Cl.
*A61M 5/32* (2006.01)
*A61M 5/00* (2006.01)
*A61M 25/18* (2006.01)
*A61M 39/00* (2006.01)

(52) U.S. Cl. ........................ 604/174; 604/256; 604/533
(58) Field of Classification Search ................ 604/107, 604/500, 174, 246, 178, 256, 533–527, 534–537, 604/910, 250, 164.1, 164.07, 252, 171, 270, 604/164.02, 523, 104, 93.01, 164.01
See application file for complete search history.

(56) References Cited

U.S. PATENT DOCUMENTS 3,908,663 A * 9/1975 Viek .......................... 600/581

(Continued)

FOREIGN PATENT DOCUMENTS

EP          976 418          2/2000

*Primary Examiner*—Nicholas D. Lucchesi
*Assistant Examiner*—Matthew F. DeSanto
(74) *Attorney, Agent, or Firm*—Kriegsman & Kriegsman

(57) ABSTRACT

A medical catheter assembly including a removable inner sleeve. In one embodiment, the assembly is a low profile percutaneous endoscopic gastrostomy (PEG) device and comprises a body, a clamp, a feeding tube, a cap and an inner sleeve assembly. The body includes a base portion and a sleeve portion, the base portion being dimensioned to engage the skin of a patient and having a transverse bore, the sleeve portion extending upwardly from the base portion and having a longitudinal slot aligned with the transverse bore and a transverse slot intersecting the longitudinal bore. The clamp, which is slidably mounted on the base portion and across the transverse slot of the sleeve, comprises a plate having a transverse opening. The transverse opening has a wide region and a narrow region, the two regions being alternately alignable with the longitudinal bore to open and to close, respectively, the feeding tube. The feeding tube has a distal end adapted to be anchored to the inside of a patient and a proximal end inserted up through the base portion and the sleeve portion, including the transverse opening of the clamp situated within the sleeve, and then inverted over the top edge of the sleeve. The cap is then mounted on top of the sleeve so as to secure the inverted end of the catheter to the exterior of the sleeve. The cap is provided with an opening through which access to the catheter may be gained. An inner sleeve, sized to engage the inside surface of the feeding tube, is removably inserted through the cap and the feeding tube, the inner sleeve having a proximal end to which a tubular fitting is secured. Food and/or medications are dispensed to the patient through the fitting and the inner sleeve and, in this manner, prevent clogging of the feeding tube.

24 Claims, 13 Drawing Sheets

U.S. PATENT DOCUMENTS

| | | |
|---|---|---|
| 3,926,187 A | 12/1975 | Iglesias |
| 3,938,530 A * | 2/1976 | Santomieri .................. 604/105 |
| 3,946,741 A * | 3/1976 | Adair .................... 604/164.01 |
| 4,306,545 A | 12/1981 | Ivan et al. |
| 4,390,017 A | 6/1983 | Harrison et al. |
| 4,417,890 A | 11/1983 | Dennehey et al. |
| 4,424,833 A | 1/1984 | Spector et al. |
| 4,473,369 A | 9/1984 | Lueders et al. |
| 4,557,261 A | 12/1985 | Rügheimer |
| 4,774,944 A | 10/1988 | Mischinski |
| 4,826,477 A | 5/1989 | Adams |
| 4,834,712 A | 5/1989 | Quinn et al. |
| 4,863,438 A | 9/1989 | Gauderer et al. |
| 4,944,732 A | 7/1990 | Russo |
| 5,007,900 A | 4/1991 | Picha et al. |
| 5,026,352 A | 6/1991 | Anderson |
| 5,071,405 A | 12/1991 | Piontek et al. |
| 5,100,394 A | 3/1992 | Dudar et al. |
| 5,112,310 A | 5/1992 | Grobe |
| 5,158,569 A | 10/1992 | Strickland et al. |
| 5,167,627 A | 12/1992 | Clegg et al. |
| 5,259,399 A | 11/1993 | Brown |
| 5,267,983 A | 12/1993 | Oilschlager et al. |
| 5,290,250 A | 3/1994 | Bommarito |
| 5,358,488 A | 10/1994 | Suriyapa |
| 5,458,583 A * | 10/1995 | McNeely et al. ...... 604/103.13 |
| 5,488,949 A | 2/1996 | Kreifels et al. |
| 5,514,112 A | 5/1996 | Chu et al. |
| 5,527,280 A * | 6/1996 | Goelz ........................ 604/178 |
| 5,549,657 A | 8/1996 | Stern et al. |
| 5,720,734 A | 2/1998 | Copenhaver et al. |
| 5,836,924 A | 11/1998 | Kelliher et al. |
| 6,095,997 A | 8/2000 | French et al. |
| 6,666,853 B1 * | 12/2003 | Chu et al. ................... 604/533 |

* cited by examiner

MEDICAL CATHETER ASSEMBLY INCLUDING A REMOVABLE INNER SLEEVE AND METHOD OF USING THE SAME

BACKGROUND OF THE INVENTION

The present invention relates generally to medical catheters, such as gastrostomy feeding tubes, and relates more particularly to medical catheter assemblies, such as percutaneous endoscopic gastrostomy (PEG) devices.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the longterm. Accordingly, the most common approach to the long-term feeding of such patients involves gastrostomy, i.e., the creation of a feeding tract or stoma between the stomach and the upper abdominal wall. Feeding is then typically performed by administering food through a catheter or feeding tube that has been inserted into the feeding tract, with the distal end of the feeding tube extending into the stomach and being retained therein by an internal anchor or bolster and the proximal end of the feeding tube extending through the abdominal wall.

Although gastrostomies were first performed surgically, most gastrostomies are now performed using percutaneous endoscopy. In one type of percutaneous endoscopic gastrostomy (PEG) technique, the distal end of an endoscope is inserted into a patient's mouth and is passed through the esophagus into the stomach. After distension of the stomach by inflation, an entry site on the abdomen is identified and an incision can be made. A needle, with an outer cannula, is inserted through the entry site across the abdominal and gastric walls. While keeping the cannula in place, the needle is removed, and a flexible wire is passed through the cannula into the stomach and into a snare loop extended from the distal end of the endoscope. The endoscopic snare loop is then used to grasp the wire, the cannula is released, and the endoscope and wire are withdrawn through the esophagus and mouth of the patient. A silicone gastrostomy feeding tube, the distal end of which is attached to a silicone, dome-shaped internal bolster, is then secured to the wire and is pulled from its proximal end through the esophagus and into the stomach until the internal bolster engages the stomach wall and the feeding tube extends through the stomach and abdominal walls, with the proximal end of the feeding tube extending approximately one foot beyond the abdominal wall. (Over a period of several days following implantation of the feeding tube, a stable stoma tract forms around the feeding tube between the gastric and abdominal walls.)

With the internal bolster in place against the gastric wall, an external bolster is typically secured to the feeding tube to engage the abdomen so as to prevent longitudinal movement of the feeding tube within the stoma tract. Additionally, a "Y-port" adapter is typically attached to the proximal end of the feeding tube, the Y-port adapter being adapted to receive a pair of connector tips through which food and/or medications may be dispensed. In addition, a detachable locking clip is typically secured to the feeding tube at a point between the external bolster and the Y-port adapter to prevent gastric fluids from escaping through the proximal end of the feeding tube when the feeding tube is not in use.

Alternative techniques for implanting gastrostomy feeding tubes using percutaneous endoscopic gastrostomy are disclosed in U.S. Pat. No. 5,112,310, inventor Grobe, which issued May 12, 1992, and U.S. Pat. No. 5,167,627, inventors Clegg et al., which issued Dec. 1, 1992, both of which are incorporated herein by reference.

Although gastrostomy feeding tubes of the type described above work well for their intended purpose, many active patients find the nearly one foot length of tubing that extends externally to be unwieldy, difficult to conceal and susceptible to being inadvertently pulled on. As can readily be appreciated, these conditions are potential sources of physical and/or psychological trauma to the patient. Consequently, a variety of low-profile replacement tube assemblies (also referred to in the art as low-profile replacement PEG devices) have been designed for implantation within the stoma tract following the removal of an initially-implanted gastrostomy feeding tube. Such replacement assemblies are referred to as being "low-profile" because they are considerably more compact externally than the above-described initially-implanted gastrostomy feeding tube assemblies.

An example of a low-profile replacement PEG device is disclosed in U.S. Pat. No. 4,944,732, inventor Russo, which issued Jul. 31, 1990, and which is incorporated herein by reference. The low-profile replacement PEG device of said patent comprises a deformable, conical tip portion having at least one side aperture therethrough, a tube portion which extends rearwardly from the tip portion, a fitting portion on the rear end of the tube portion, a removable valve portion in the fitting portion and a flange portion which extends outwardly from the fitting portion. The device is adapted to be installed in a patient so that the tube portion extends through a pre-established stoma with the tip portion located in the patient's stomach and with the fitting portion and the flange portion engaging the skin of the patient adjacent the stoma.

The deformable tip portion of the above-described low-profile replacement PEG device functions as an internal bolster to anchor its associated tube portion in a patient's stomach. To implant and/or remove the aforementioned tube portion from a patient's stomach, an obturator or similar device is typically inserted through the tube portion and is used to elongate or otherwise deform the tip portion in such a way as to permit the tip portion to fit through the stoma. Removal of the obturator from the tip portion then permits the tip portion to expand to its original shape for anchoring.

Another type of low-profile replacement PEG device uses an inflatable balloon, instead of a deformable tip portion, as an internal bolster to retain the distal end of its associated tube within a patient's stomach. To implant such a device in a patient, the inflatable balloon is deflated, the distal end of the tube portion is inserted through the stoma, and the balloon is then inflated. To remove the implanted device from a patient, the balloon is deflated and the tube is then withdrawn from the stoma.

Further examples of low-profile replacement PEG devices are disclosed in U.S. Pat. No. 4,863,438, inventors Gauderer et al., which issued Sep. 5, 1989; and U.S. Pat. No. 5,720,734, inventors Copenhaver et al., which issued Feb. 24, 1998, both of which are incorporated herein by reference.

Although low-profile replacement PEG devices are less awkward and bulky than initially-implanted gastrostomy tube assemblies, the use of such low-profile replacement PEG devices suffers from its own set of shortcomings. One such shortcoming is that the implantation of a low-profile replacement PEG device must be preceded by the removal of an initially-implanted gastrostomy tube. Such removal typically involves pulling on the proximal end of the gastrostomy tube until the internal bolster fails and is drawn through the stoma. As can readily be appreciated, such a procedure can be quite painful to the patient and can result in damage to the stoma, thereby delaying when the replacement device can be implanted.

Another shortcoming of many low-profile replacement PEG devices is that such devices typically do not last as long as initially-implanted gastrostomy tube assemblies (most commonly due to failure of their internal anchoring mechanisms or due to clogging or other failure of their valve mechanisms) and, therefore, must be replaced more frequently than is the case with initially-implanted gastrostomy tube assemblies.

Still another shortcoming of many low-profile replacement PEG devices is that such devices are typically not adjustable in length. This can be problematic because there is often an appreciable variation in stoma length from patient to patient. Consequently, it is typically necessary, after removal of the initially-implanted tube and prior to implantation of the replacement device, to measure the length of the stoma and then to select a replacement device having an appropriate length. As can readily be appreciated, this approach requires that there be made available an inventory of replacement devices of varying lengths.

In order to avoid the aforementioned shortcomings of low-profile replacement PEG devices while, at the same time, avoiding the above-described problems associated with having a gastrostomy tube extend externally for a substantial length, there have recently been devised a number of adaptors designed for use in converting an initially-implanted gastrostomy tube into a low-profile PEG device. One such adaptor is disclosed in U.S. Pat. No. 5,549,657, inventors Stern et al., which issued Aug. 27, 1996, and which is incorporated herein by reference. According to said patent, an adaptor is disclosed therein that is designed for use with a gastostomy feeding tube which has been inserted by means of conventional endoscopic procedures and which has been cut to a desired length by a surgeon. The adaptor is said to comprise an anti-reflux valve assembly having a stem which can be plugged into the open end of the feeding tube. The valve assembly is said to contain a seal which functions as a one-way valve to prevent reflux of gastric contents but which permits the introduction of feeding solution into the feeding tube. A clamp is placed around the feeding tube and the valve stem and is locked into place to secure the valve assembly to the feeding tube at a location flush with the patient's skin. A silicone cover is placed around the clamp to protect the patient from skin irritation caused by the clamp and also to protect the clamp and valve assembly from contaminants.

One problem that the present inventors have noted with regard to low-profile PEG devices, both of the above-described replacement variety and of the above-described convertible variety, is that the feeding tubes of such devices have a tendency, over time, to become clogged with food, gastric contents or other debris. Such clogging of a gastrostomy feeding tube is clearly undesirable as it impedes the delivery of food and/or medications to the patient therethrough. Consequently, once a gastrostomy feeding tube becomes clogged, it must be cleaned or replaced. Cleaning of the tube typically involves pushing the clogged material back into the stomach or, more desirably, carefully scooping the clogged material out of the tube through its proximal end. Because a patient typically cannot see down into the tube, due to the location and orientation of the tube on the patient, the patient typically must scoop the clogged material out of the tube by feel. As can readily be appreciated, such a technique can be difficult to perform successfully.

In the event that the clogged material cannot be sufficiently removed from the tube, either by the patient or by someone else, the gastrostomy feeding tube must be removed from the patient and replaced. As noted above, the removal of a gastrostomy feeding tube, particularly an initially-implanted gastrostomy feeding tube, often requires medical attention and can cause discomfort and/or injury to the patient. In addition, as noted above, the replacement of an initially-implanted gastrostomy feeding tube with a replacement PEG device leads to its own set of possible pitfalls.

One approach that has been used to prevent the clogging of gastrostomy feeding tubes has been to position a reflux valve at the distal end of the tube near the internal bolster. The reflux valve is typically a pivotally mounted flap of rubber that blocks fluids from flowing back up through the feeding tube. An example of such a reflux valve is disclosed in U.S. Pat. No. 4,863,438. Unfortunately, over time, the reflux valve, itself, starts to collect debris, causing it to fail. Moreover, the presence of a reflux valve in the lumen of the feeding tube makes the feeding tube even more difficult to clean.

SUMMARY OF THE INVENTION

It is an object of the present invention to provide a novel medical catheter assembly.

It is another object of the present invention to provide a medical catheter assembly as described above that overcomes at least some of the problems described above in connection with existing medical catheter assemblies, particularly low profile PEG devices.

Therefore, according to one aspect of the invention, there is provided a medical catheter assembly comprising (a) a medical catheter, said medical catheter having a proximal end, a distal end and a longitudinal bore, said distal end being shaped to define an internal bolster; and (b) an inner sleeve, said inner sleeve having a proximal end and a distal end, at least a portion of said inner sleeve being removably disposed within said longitudinal bore of said medical catheter.

In a preferred embodiment, the medical catheter assembly is a low profile percutaneous endoscopic gastrostomy (PEG) device comprising a body, a clamp, a feeding tube, a cap and an inner sleeve assembly. The body includes a base portion and a sleeve portion, the base portion being dimensioned to engage the skin of a patient and having a transverse bore, the sleeve portion extending upwardly from the base portion and having a longitudinal slot aligned with the transverse bore and a transverse slot intersecting the longitudinal bore. The clamp, which is slidably mounted on the base portion and across the transverse slot of the sleeve, comprises a plate having a transverse opening. The transverse opening has a wide region and a narrow region, the two regions being alternately alignable with the longitudinal bore to open and to close, respectively, the feeding tube. The feeding tube has a distal end adapted to be anchored to the inside of a patient and a proximal end inserted up through the base portion and the sleeve portion, including the transverse opening of the clamp situated within the sleeve, and then inverted over the top edge of the sleeve. The cap is then mounted on top of the sleeve so as to secure the inverted end of the catheter to the exterior of the sleeve. The cap is provided with an opening through which access to the catheter may be gained. An inner sleeve, sized to engage the inside surface of the feeding tube along its entire non-inverted length, is removably inserted through the cap and the feeding tube, the inner sleeve having a proximal end to which a tubular fitting is secured. Food and/or medications are dispensed to the patient through the fitting and the inner sleeve. In this manner, because the feeding tube is not exposed to the materials being dispensed or to gastric materials from the patient, clogging of the feeding tube is minimized. When, after time, the inner sleeve becomes clogged, it may be removed from the feeding tube and repaired (i.e, cleaned) or replaced. Alternatively, after having been removed, the inner sleeve may not be repaired or replaced, and the feeding tube may simply be used without an inner sleeve. In any event, use of the inner sleeve, for any extent of time, increases the lifetime of the feeding tube.

According to another aspect of the invention, there is provided a medical catheter assembly comprising (a) a medical catheter, said medical catheter having a proximal end, a distal end and a longitudinal bore, said distal end being shaped to define an internal bolster; and (b) a solid body, at least a portion of said solid body being removably disposed within said longitudinal bore of said medical catheter.

The aforementioned medical catheter assembly differs from the previous medical catheter assembly in that the solid body is installed in the medical catheter (e.g., gastrostomy feeding tube) only between uses and must be removed from the medical catheter during use so that materials may pass through the longitudinal bore of the medical catheter.

The present invention is also directed to methods of draining materials from a patient and administering food and/or medications to a patient.

For purposes of the present specification and claims, relational terms like "top," "bottom," "upper," and "lower" are used to describe the present invention in an context in which the invention is secured to a catheter extending upwardly out of a patient. It is to be understood that, by orienting a patient such that the catheter extends outwardly in a direction other than upwardly, the directionality of the invention will need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute apart of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

Figure 1:
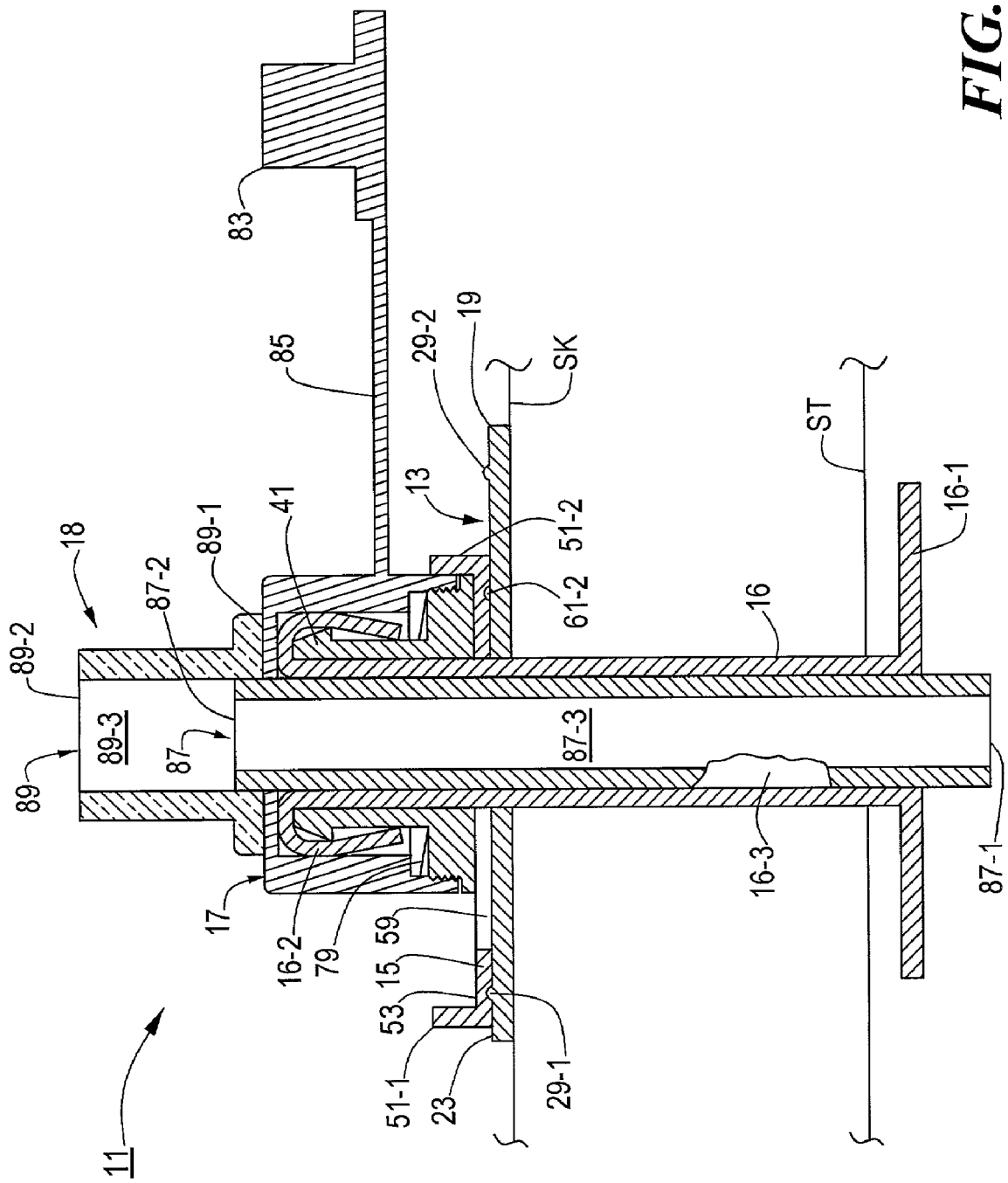
FIG. 1 is a section view, broken away in part, of a first embodiment of a low profile medical catheter assembly constructed according to the teachings of the present invention, the low profile medical catheter assembly being shown implanted in a patient.

Referring now to FIG. 1, there is shown a section view, broken away in part, of a first embodiment of a low profile medical catheter assembly constructed according to the teachings of the present invention, said low profile medical catheter assembly being represented generally by reference numeral 11.

Assembly 11, which is shown implanted in a patient as a low profile, convertible, percutaneous endoscopic gastrostomy (PEG) device, comprises a body 13, a clamp 15, a gastrostomy feeding tube 16, a cap 17, and an inner sleeve assembly 18.

Figure 2B:
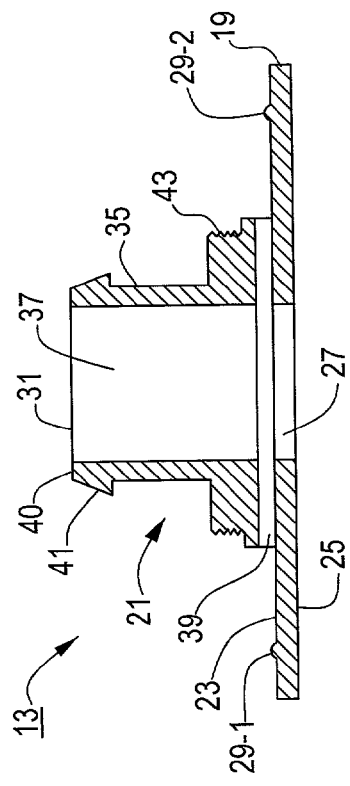
FIGS. 2(a) and 2(b) are top and section views of the body shown in FIG. 1, the transverse slot of the body being shown in dotted lines in FIG. 2(a)
Figure 2A:
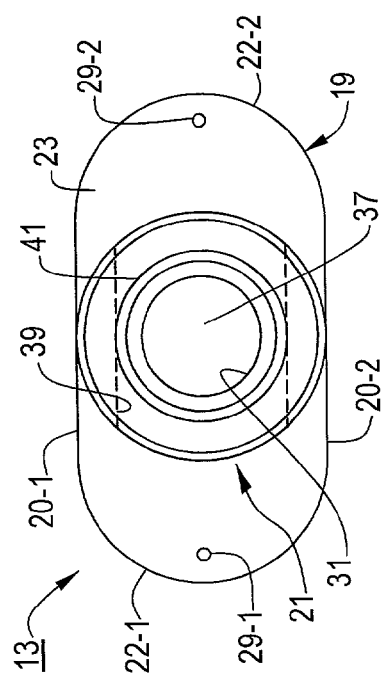

Referring now to FIGS. 1, 2(a) and 2(b), body 13, which is a unitary structure preferably made of molded medical grade plastic, is shaped to include a base 19 and a sleeve 21. Base 19, which is appropriately sized to engage the skin SK of the patient surrounding a stoma tract so as to serve as an external bolster, is a quasi-rectangular member having a pair of straight sides 20-1 and 20-2, a pair of rounded ends 22-1 and 22-2, a top surface 23, a bottom surface 25 and a centrally-disposed transverse bore 27. A pair of detents 29-1 and 29-2 are formed on top surface 23 along its longitudinal centerline, the purpose of detents 29-1 and 29-2 to be discussed below.

Sleeve 21 is an elongated tubular member that extends upwardly from top surface 23, sleeve 21 having an open top end 31, an open bottom end, a generally circular side wall 35, a longitudinal bore 37 and a transverse slot 39. For reasons to be discussed below, the top portion of side wall 35 is shaped to define an upwardly-directed external barb 41. For reasons also to be discussed below, an intermediate portion of side wall 35 is shaped to include an external helical thread 43. Longitudinal bore 37 is aligned with transverse bore 27 of base 19 and is substantially equal in diameter thereto. Transverse slot 39, which is formed in the bottom portion of side wall 35 and runs generally parallel to the length of base 19, intersects longitudinal bore 37 for reasons to be discussed below.

Figure 3:
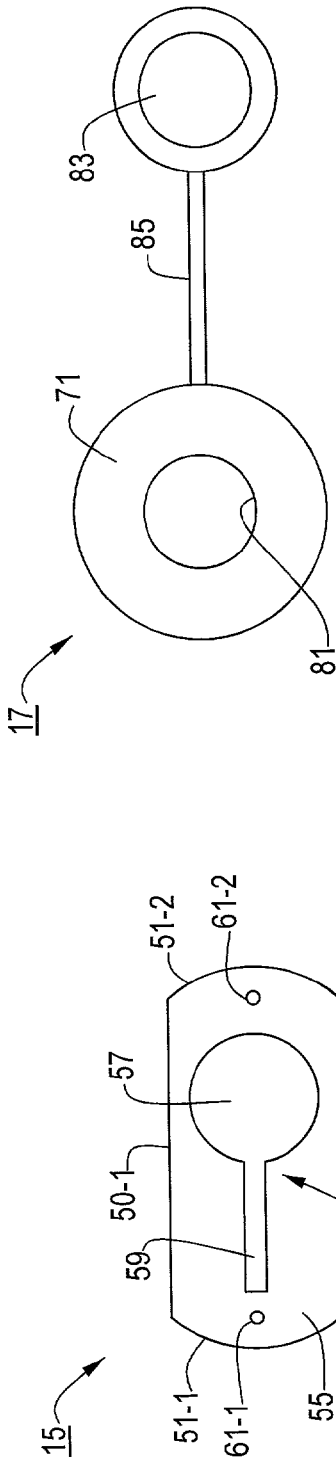
FIG. 3 is a bottom view of the clamp shown in FIG. 1.

Referring now to FIGS. 1 and 3, clamp 15, which is preferably made of molded medical grade plastic, is an elongated, quasi-rectangular slide having a pair of straight sides 50-1 and 50-2, a pair of rounded, turned-up ends 51-1 and 51-2, a top surface 53, a bottom surface 55, and a transverse opening 56. Transverse opening 56 comprises a wide circular region 57 and a narrow slit region 59. For reasons to become apparent below, wide circular region 57 is substantially equal in size to bores 27 and 37 whereas narrow slit region 59 is much smaller in size than bores 27 and 37. A pair of recesses 61-1 and 61-2 are provided in bottom surface 55 of clamp 15, recess 61-1 being adapted to receive detent 29-1 to maintain clamp 15, when desired, in an open position, recess 61-2 being adapted to receive detent 29-2 to maintain clamp 15, when desired, in a closed position.

Clamp 15 is slidably mounted on base 19 and across slot 39 and is movable between (i) an open position in which circular region 57 is aligned with bores 27 and 37, and detent 29-1 is received in recess 61-1 and (ii) a closed position in which slit region 59 is aligned with bores 27 and 37, and detent 29-2 is received in recess 61-2.

Referring now to FIG. 1, gastrostomy feeding tube 16, which may be a conventional gastrostomy feeding tube, comprises an open distal end 16-1, an open proximal end 16-2 and a longitudinal bore 16-3. Tube 16 is appropriately dimensioned for insertion through the stoma tract of the patient and through bore 27 of base 19, opening 56 of clamp 15 and bore 37 of sleeve 21, with distal end 16-1 being shaped to define an internal bolster adapted to engage the stomach ST of the patient and with proximal end 16-2 being folded over top end 31 of sleeve 21 and extending downwardly over barb 41. When clamp 15 is in its open position, tube 16 is disposed within opening 57, opening 57 allowing tube 16 to open to its full inner diameter. When, however, clamp 15 is in its closed position, tube 16 is disposed within slit 59, slit 59 compressing tube 16 to closure.

Figure 4A:
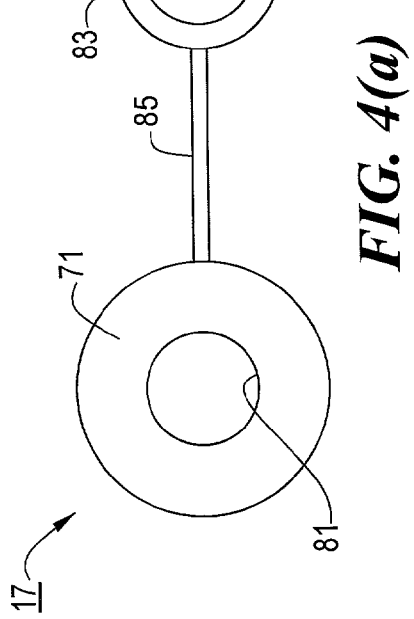
FIGS. 4(a) and 4(b) are top and section views of the cap shown in FIG. 1.
Figure 4B:
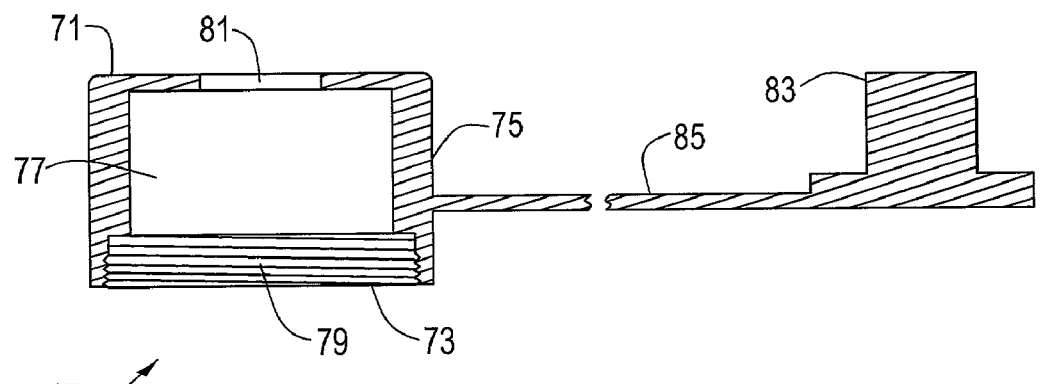

Referring now to FIGS. 1, 4(a) and 4(b), cap 17, which is a unitary member preferably made of molded medical grade plastic, comprises a top wall 71, an open bottom 73, a circular side wall 75 and a cylindrical cavity 77, cylindrical cavity 77 being circumferentially bounded by side wall 75. The bottom portion of side wall 75 has a decreased cross-sectional thickness, and a helical thread 79 is formed on the inside surface thereof so that cap 17 may be removably mounted over proximal end 16-2 of tube 16 and onto body 13, with thread 79 matingly engaging thread 43 of sleeve 21. A transverse opening 81 having a diameter substantially equal to bore 16-3 of tube 16 is provided in top wall 71 and is aligned with bore 16-3.

It should be noted that cap 17 serves to secure proximal end 16-2 of tube 16 against barb 41 and against the top edge 40 of sleeve 21, thereby increasing the grip strength of adaptor 11 to at least 18 pounds. It is also to be noted that the compression of tube 16 by cap 17 against sleeve 21 creates a tight seal between assembly 18 and tube 16.

Cap 17 further comprises a plug 83, plug 83 being adapted for removable insertion directly into tube 16 through opening 81 when assembly 18 is removed therefrom. Plug 83 is connected to side wall 75 by a strap 85.

Referring now to FIG. 1, inner sleeve assembly 18 comprises an inner sleeve 87 and a fitting 89. Inner sleeve 87, which is removably inserted through opening 81 of cap 17 and bore 16-3 of tube 16, is a tubular member having a distal end 87-1, a proximal end 87-2 and a longitudinal bore 87-3. Sleeve 87 is appropriately dimensioned so that its distal end 87-1 extends just beyond distal end 16-1 of tube 16 (so as not to interfere with stomach function) and so that, along that portion of its length disposed within tube 16, it is sealed against the inside of tube 16 to prevent materials from coming into direct contact with the inside of tube 16. Fitting 89 is a tubular member having an open distal end 89-1, an open proximal end 89-2 and a longitudinal bore 89-3. Distal end 89-1 is secured to proximal end 87-2 of sleeve 87 and is sized greater than opening 81 of cap 17 to delimit downward translational movement of sleeve 87. Proximal end 89-2 of fitting 89 is adapted to removably receive a food/medications delivery tube or drainage tube (not shown). As can readily be appreciated, fitting 89 could be modified so as to be adapted for connection at its proximal end to devices other than tubes.

Figure 5A:
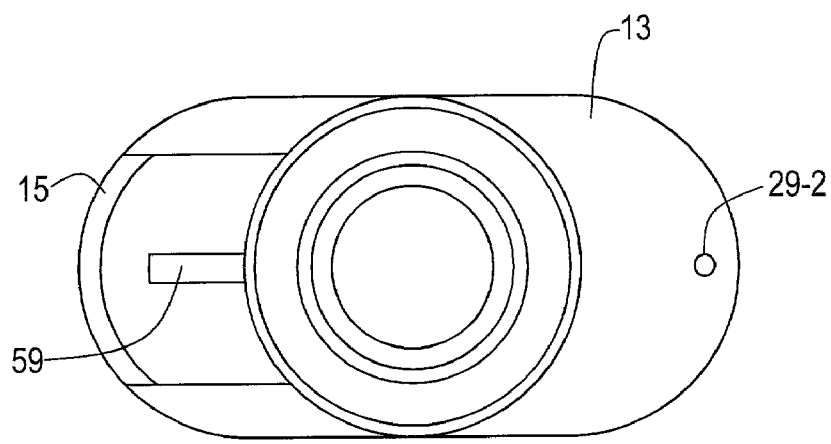
FIGS. 5(a) and 5(b) are top and section views, respectively, of the body and the clamp of FIG. 1 shown in an assembled state, with the clamp in an open position.
Figure 5B:
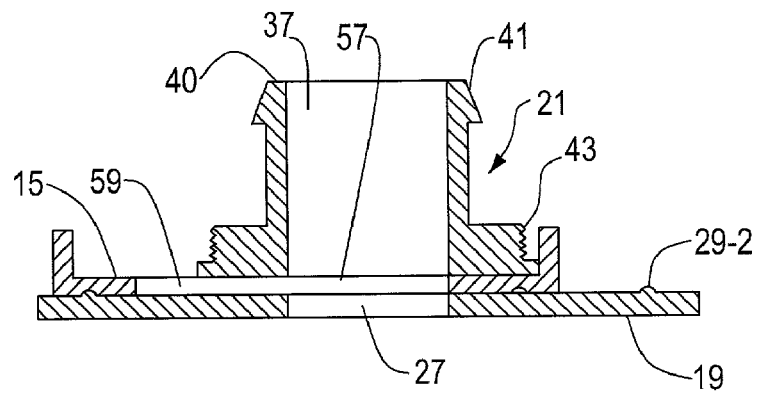
Figure 6:
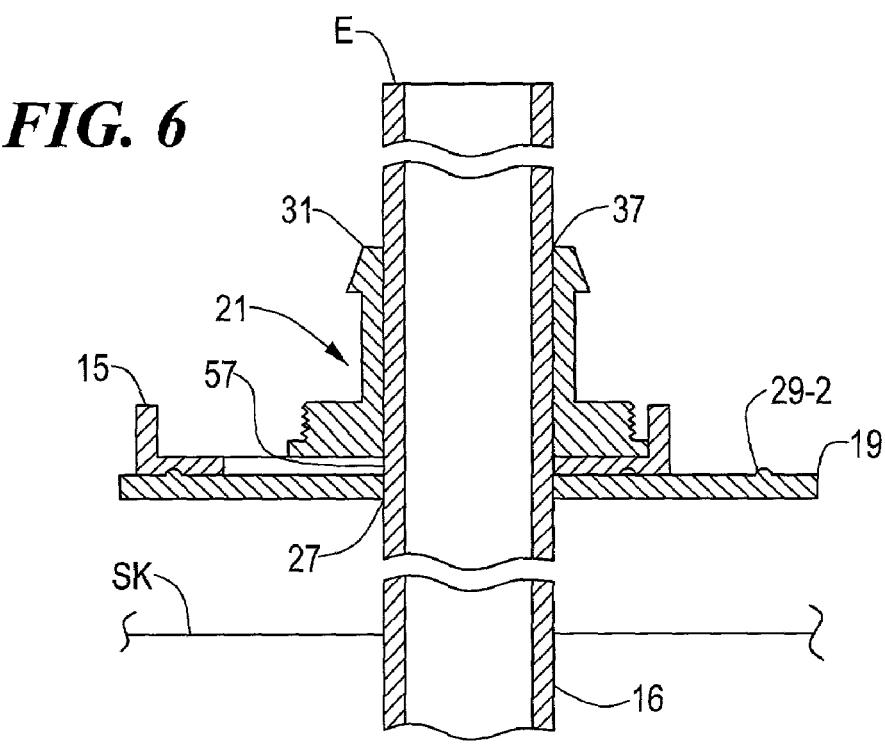
FIG. 6 is a section view showing the proximal end of an implanted gastrostomy feeding tube inserted up through the assembly of FIGS. 5(a) and 5(b)
Figure 7:
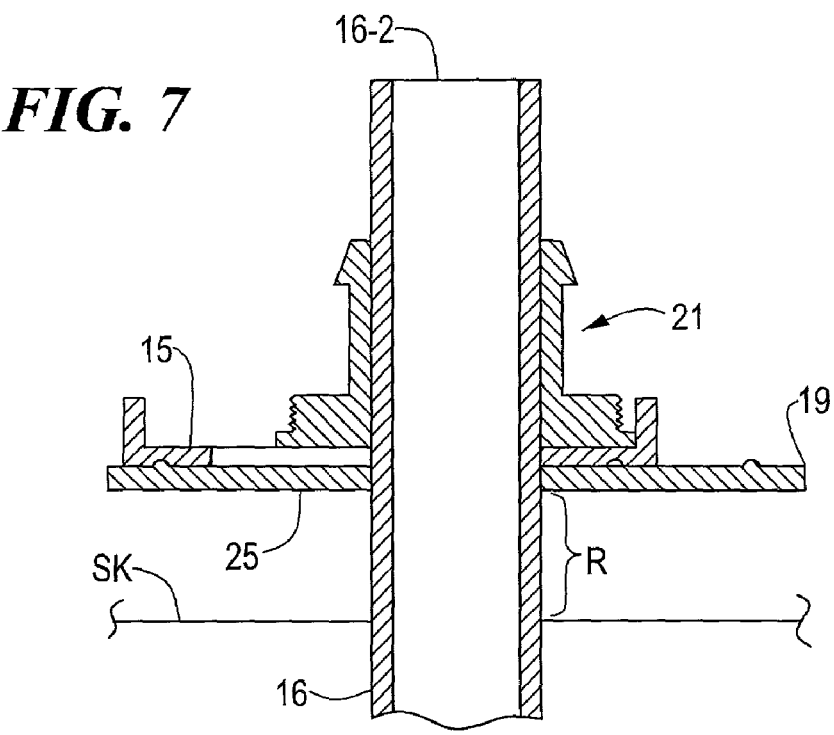
FIG. 7 is a section view showing the implanted gastrostomy feeding tube cut to a desired length following insertion through the assembly of FIGS. 5(a) and 5(b)

Where, as in the present case, assembly 11 is a convertible PEG device, its manner of being assembled may be as follows: First, as seen in FIGS. 5(a) and 5(b), with cap 17 removed from body 13, clamp 15 is positioned relative to body 13 so that circular region 57 is aligned with bores 27 and 37 and detent 29-1 is received in recess 61-1 (i.e., clamp 15 is placed in its open position). Next, as seen in FIG. 6, the proximal end E of an implanted gastrostomy feeding tube 16 is inserted up through bore 27, circular region 57, and bore 37, respectively, and extends for a distance beyond open top end 31 of sleeve 21. Next, as seen in FIG. 7, tube 16 is cut to an appropriate length to yield proximal end 16-2 and to permit tube 16 to be attached to body 13 in a low profile orientation proximate to the patient's skin SK while still reserving a tubing length R for stomach expansion and for cleaning under the bottom of base 19.

Figure 9:
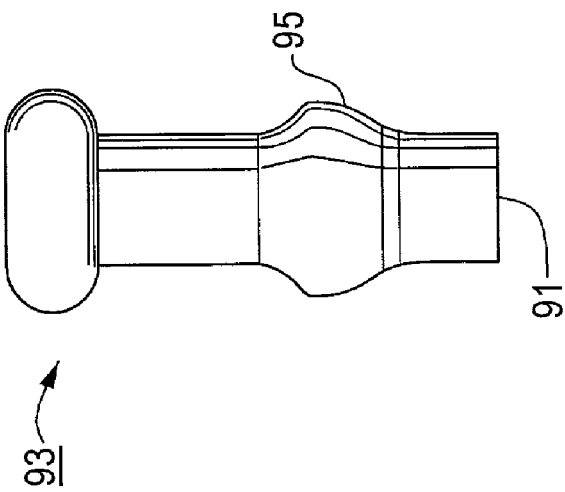
FIG. 9 is a front view of the tool of FIG. 8.
Figure 8:
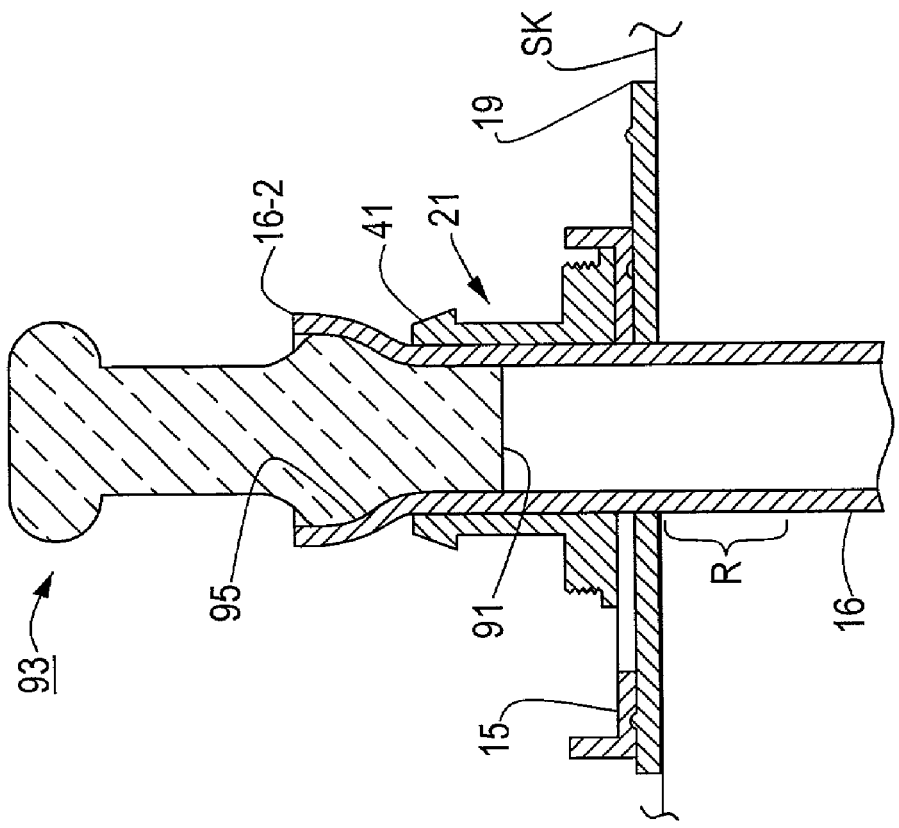
FIG. 8 is a section view showing the insertion of the bottom end of a tool down into the proximal end of the gastrostomy feeding tube of FIG. 6 so as to cause said proximal end to flare outwardly.
Figure 10:
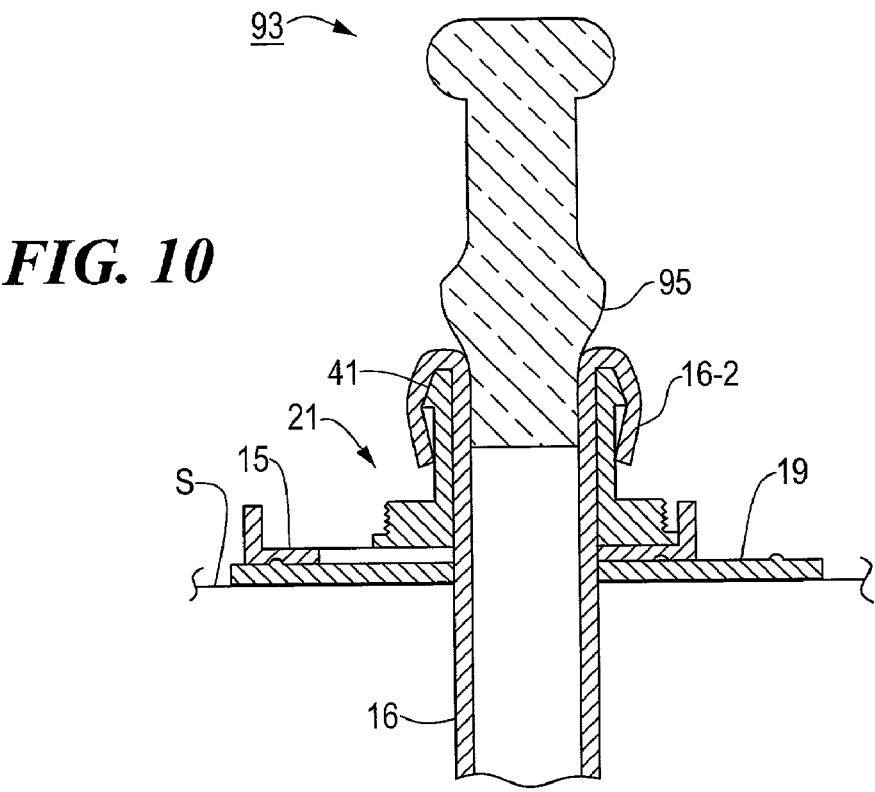
FIG. 10 is a section view showing the proximal end of the gastrostomy feeding tube of FIG. 7 folded over the barbed portion of the body.
Figure 11:
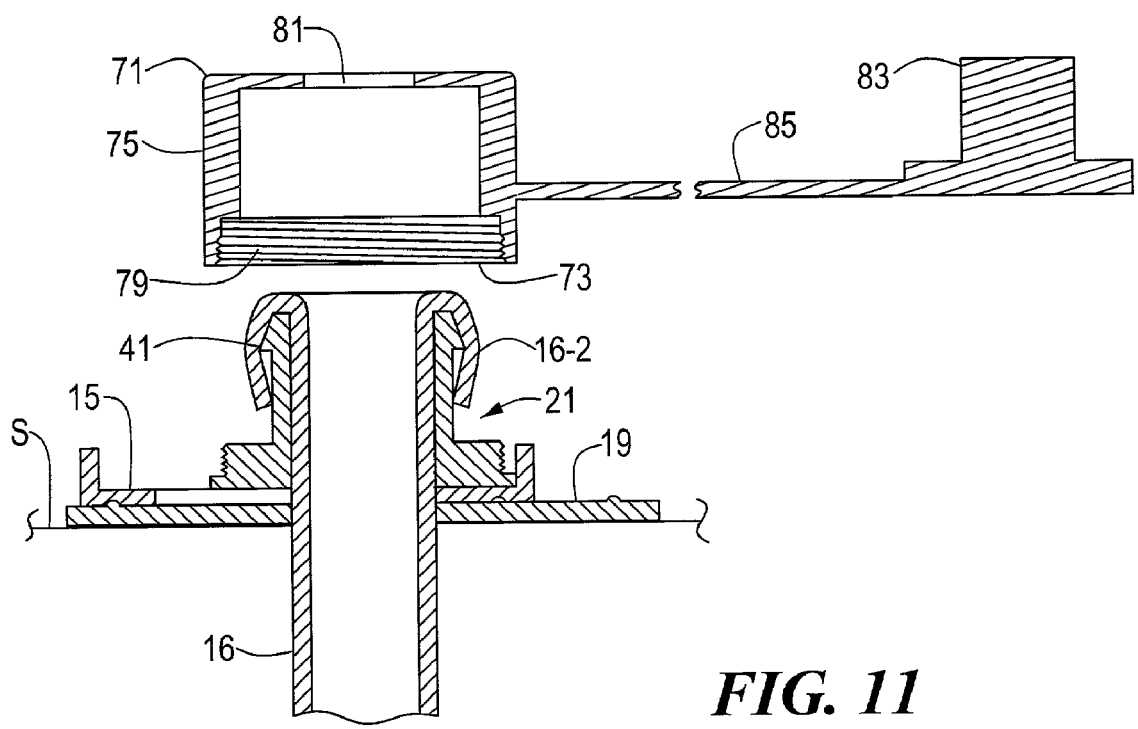
FIG. 11 is a section view showing the cap of FIG. 1 being mounted over the proximal end of the gastrostomy feeding tube and screwed to the body of the assembly of FIG. 10.

Next, as seen in FIG. 8, tubing length R is inserted into the patient and bottom surface 25 of base 19 is brought into contact with the patient's skin SK. The bottom end 91 of a tool 93 (tool 93 being shown separately in FIG. 9) is then inserted down into the proximal end 16-2 of tube 16 and into open top end 31 of sleeve 21. Tool 93 has an intermediate portion 95 that flares outwardly from bottom end 91 to a diameter that is greater than the inner diameter of sleeve 21 and that approaches the outer diameter of barb 41. Consequently, the insertion of bottom end 91 of tool 93 into proximal end 16-2 of tube 16 causes proximal end 16-2 of tube 16 to flare outwardly. Next, as seen in FIG. 10, proximal end 16-2 of tube 16 is then folded over barb 41 of sleeve 21. This may be done simply by rolling proximal end 16-2 of tube 16 down off intermediate portion 95 of tool 91 using the thumb and forefinger of one hand. As can be appreciated, the engagement of the proximal end 16-2 of the tube 16 by barb 41 inhibits, to a certain degree, withdrawal of the tube 16 from sleeve 21. Next, as seen in FIG. 11, cap 17 is positioned over proximal end 16-2 and is screwed onto sleeve 21. (It should be noted that, although cap 17 and sleeve 21 are secured to one another in the present embodiment by threads 79 and 43, respectively, cap 17 and sleeve 21 could alternatively be removably secured to one another by other suitable means.)

Figure 12:
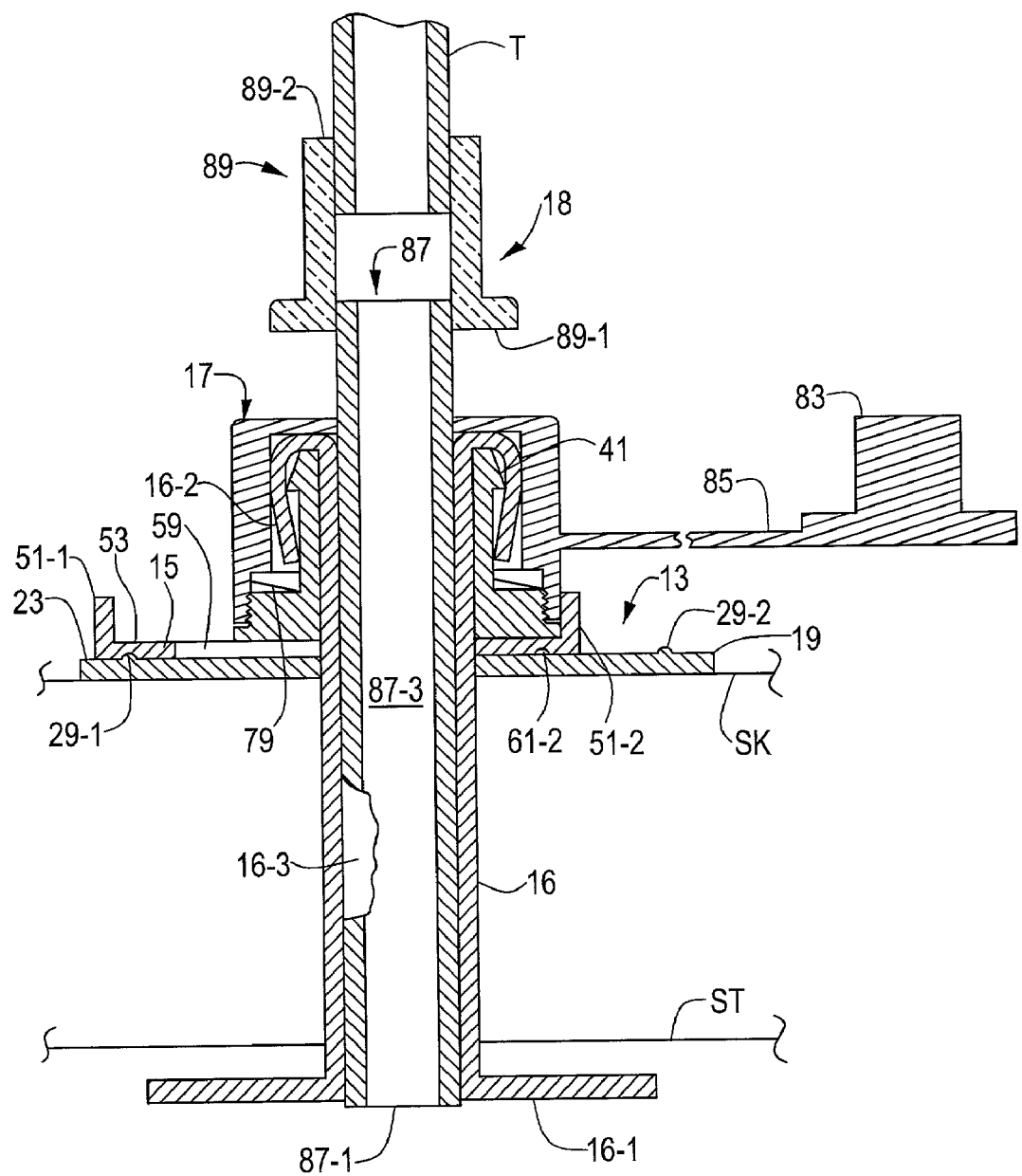
FIG. 12 is a section view showing the inner sleeve assembly of FIG. 1 being inserted through the cap and into the gastrostomy feeding tube of the assembly of FIG. 11, the inner sleeve assembly being shown connected at its proximal end to an external tube.

Next, as seen in FIG. 12, an external tube, in the form of a food/medications delivery tube T or a drainage tube, is attached to fitting 89 by insertion through proximal end 89-2, and inner sleeve 87 is inserted down through opening 81 and tube 16 until distal end 87-1 of sleeve 87 extends just beyond distal end 16-1 of tube 16. It should be noted that tube T may be secured to fitting 89 prior to the insertion of sleeve 87 through opening 81 or after the insertion of sleeve 87 through opening 81. Food and/or medications may now be dispensed to the patient from tube T through fitting 89 and sleeve 87. (Alternatively, materials from the patient's stomach may be drained through sleeve 87 and fitting 89 and into tube T.)

As can readily be appreciated, because food, medications or gastric materials are conveyed through sleeve 87, instead of being conveyed through tube 16, and because sleeve 87 forms a seal with tube 16 along the entire portion of tube 16 that would otherwise be used to convey such materials, sleeve 87 prevents tube 16 from becoming clogged directly with the materials being dispensed and/or drained. If, over time, sleeve 87 and/or fitting 89 becomes clogged, assembly 18 can simply be removed, cleaned and reinstalled or, more desirably, replaced—all without contaminating the remainder of assembly 11. The repair or replacement of inner sleeve assembly 18 is clearly preferable to replacing tube 16 which, as noted above, is a more complicated procedure. Moreover, even if one chooses not to repair or replace inner sleeve assembly 18 after one or both of sleeve 87 and fitting 89 become clogged, one can always use assembly 11 without inner sleeve assembly 18, and the lifetime of tube 16 still will be extended. Furthermore, even in the absence of a clog, inner sleeve assembly 18 can be regularly repaired (i.e., cleaned) or replaced for preventive maintenance or hygiene.

Figure 13:
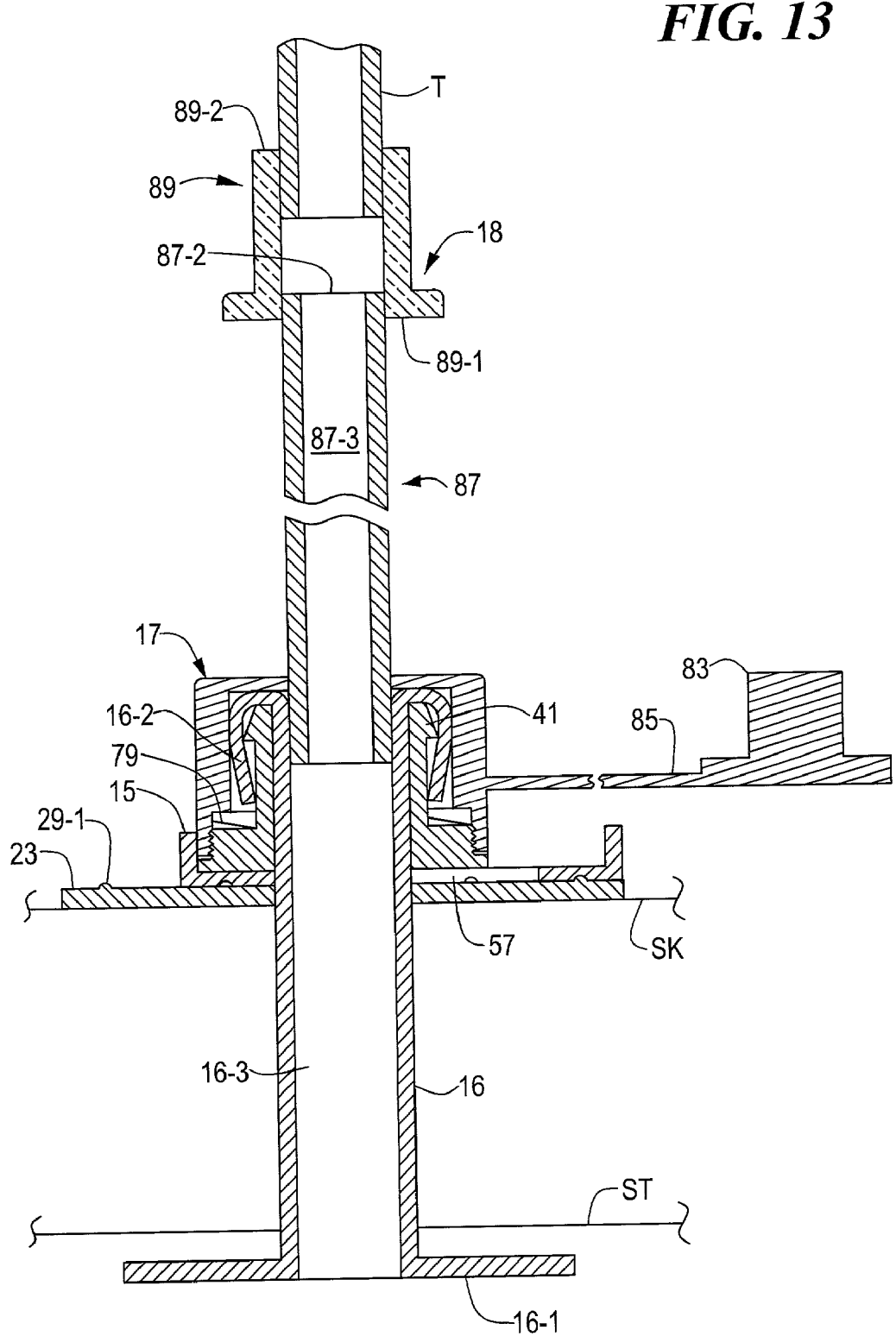
FIG. 13 is a section view of the low profile medical catheter assembly of FIG. 12, with the inner sleeve assembly and the external tube connected thereto being nearly completely disconnected from the gastrostomy feeding tube.
Figure 14:
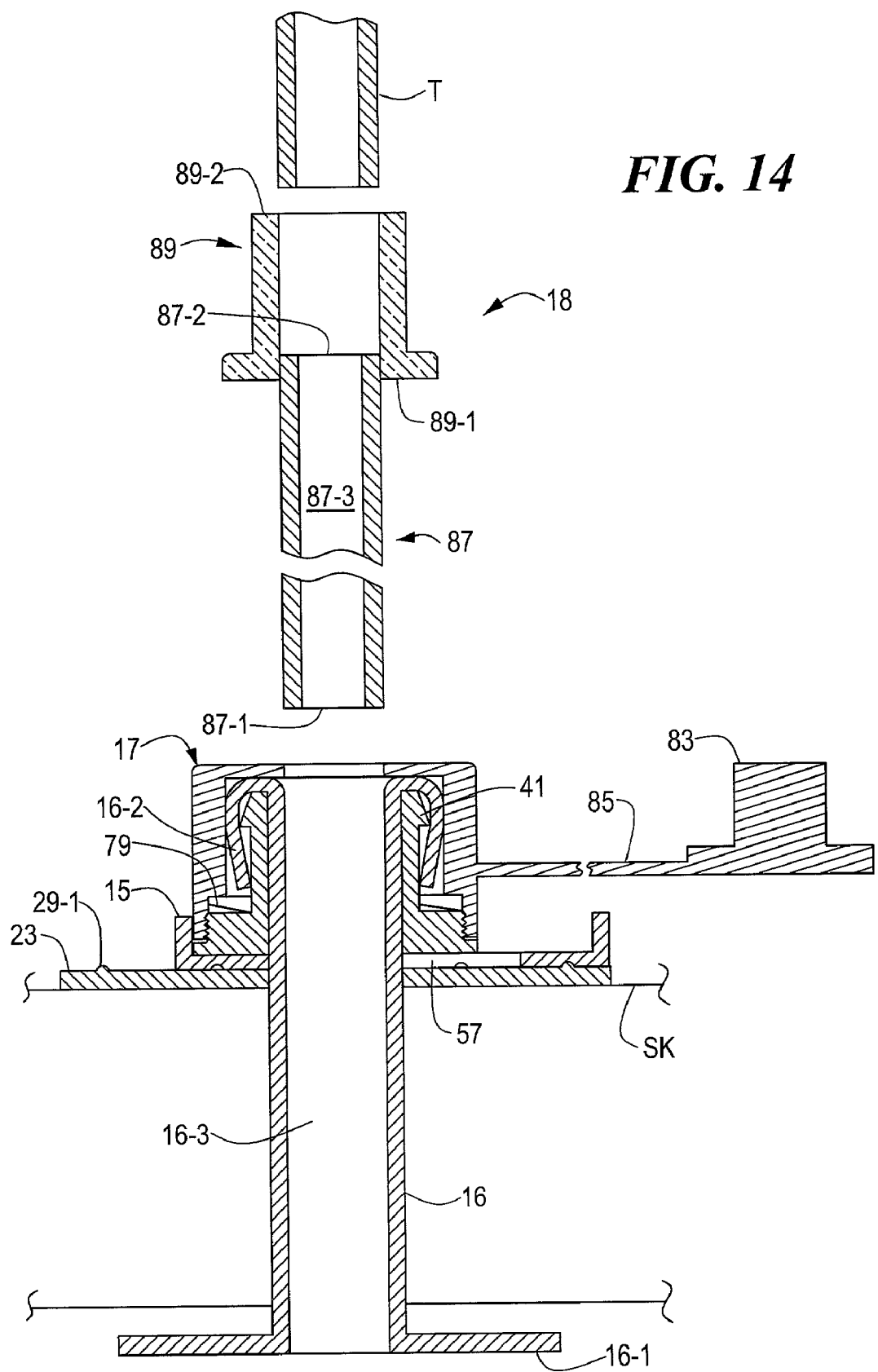
FIG. 14 is a section view of the low profile medical catheter assembly of FIG. 12, with the inner sleeve assembly and the external tube being completely disconnected from the gastrostomy feeding tube and from each other.

Referring now to FIGS. 13 and 14, when the dispensing of food and/or medications (or the drainage of the stomach) is complete, inner sleeve 87 is withdrawn through opening 81 of cap 17, and tube T is detached from fitting 89. The detaching of tube T from fitting 89 may take place prior to or after the withdrawal of sleeve 87 through opening 81. As seen best in FIG. 13, once sleeve 87 has been moved past clamp 15, clamp 15 may be moved to its closed position. (Accordingly, as can readily be appreciated, when connecting sleeve 87 to gastrostomy feeding tube 16, one may keep clamp 15 in its closed position until after sleeve 87 has been partially inserted into tube 16 and formed a seal therewith. This may serve to prevent reflux of stomach contents during installation of sleeve 87.) Once sleeve 87 has been completely removed from tube 16, plug 83 may be inserted through opening 81 and into tube 16. It should be understood that, because both plug 83 and clamp 15 may be used to open and close tube 16 to the passage of materials therethrough, one could eliminate plug 83 or clamp 15 from assembly 11.

Because tube 16 has not been brought into contact with any food (or medications), it is not necessary to flush tube 16 with water after feeding, as is conventionally done.

It should be understood that, even though assembly 11 is designed so that sleeve 87 is positioned within tube 16 during feedings (or drains) and removed between feedings (or drains), sleeve 87 could be kept in tube 16 at all times, only to be removed for cleaning or replacement once it becomes clogged. As can readily be appreciated, if sleeve 87 is used in such a manner, it may be desirable to modify clamp 15 or plug 83 to permit closure of sleeve 87 between uses.

Figure 15:
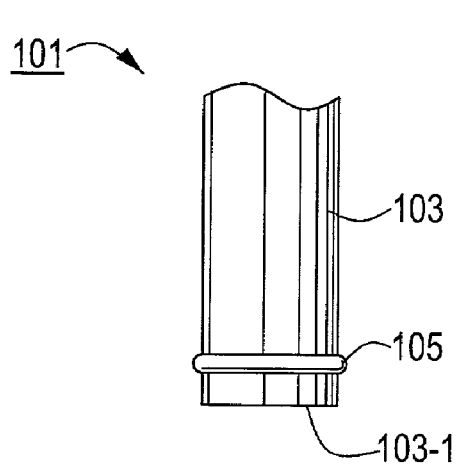
FIG. 15 is a fragmentary front view of the distal end of an alternative inner sleeve assembly adapted for use in the low profile medical catheter assembly of FIG. 1.

Referring now to FIG. 15, there is shown a fragmentary front view of the distal end of an alternative inner sleeve assembly to assembly 18, said alternative inner sleeve assembly being represented generally by reference numeral 101.

Assembly 101 is similar in many respects to assembly 18, the principal differences between the two assemblies being that (i) assembly 101 comprises, instead of inner sleeve 87, an inner sleeve 103, inner sleeve 103 having an outer diameter that is sufficiently small so as not to engage the inner diameter of tube 16; and (ii) assembly 101 further comprises a ring 105, ring 105 being mounted on inner sleeve 103 proximate to its open distal end 103-1, ring 105 serving to provide a contact seal between inner sleeve 103 and tube 16.

As can readily be appreciated, because inner sleeve 103 has a smaller outer diameter than sleeve 87, the fitting mounted on the proximate end of inner sleeve 103 must be sized accordingly.

Figure 16:
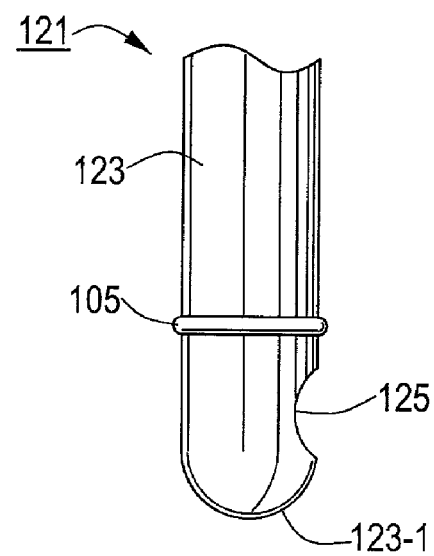
FIG. 16 is a fragmentary front view of the distal end of a second alternative inner sleeve assembly adapted for use in the low profile medical catheter assembly of FIG. 1.

Referring now to FIG. 16, there is shown a fragmentary front view of the distal end of a second alternative inner sleeve assembly to assembly 18, said second alternative inner sleeve assembly being represented generally by reference numeral 121.

Assembly 121 is similar in most respects to assembly 101, the principal differences between the two assemblies being that assembly 121 comprises, instead of inner sleeve 103, an inner sleeve 123, inner sleeve 123 having a closed distal end 123-1 and a side port 125 proximate to distal end 123-1. Distal end 123-1 is rounded so as to minimize any injury or discomfort resulting from internal contact of end 123-1 with the patient. Ring 105 is positioned just proximally of side port 125.

As can readily be appreciated, by extending the length of the inner sleeve and/or by providing a side port (and/or angling the distal end of the inner sleeve), one can deliver food and/or medications to (or drain from) a precise location within the stomach or intestine.

Figure 17:
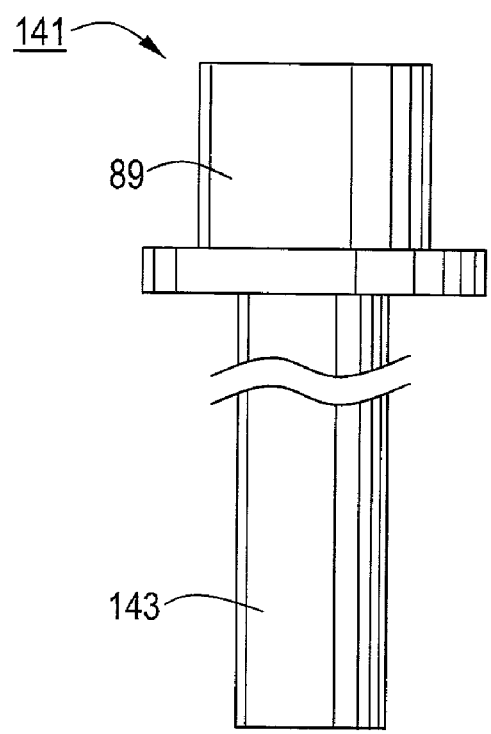
FIG. 17 is a front view of a third alternative inner sleeve assembly adapted for use in the low profile medical catheter assembly.

Referring now to FIG. 17, there is shown a fragmentary front view of the distal end of a third alternative inner sleeve assembly to assembly 18, said third alternative inner sleeve assembly being represented generally by reference numeral 141.

Assembly 141 is similar in some respects to assembly 18, the principal differences between the two assemblies being that assembly 141 comprises, instead of inner sleeve 87, a solid cylindrical body 143. Because body 143 is solid and, therefore, cannot convey materials therethrough, body 143 is designed to be positioned within tube 16 only between feedings (or drains) to prevent clogs from forming in tube 16 and must be withdrawn from tube 16 during feedings (or drains).

Figure 18:
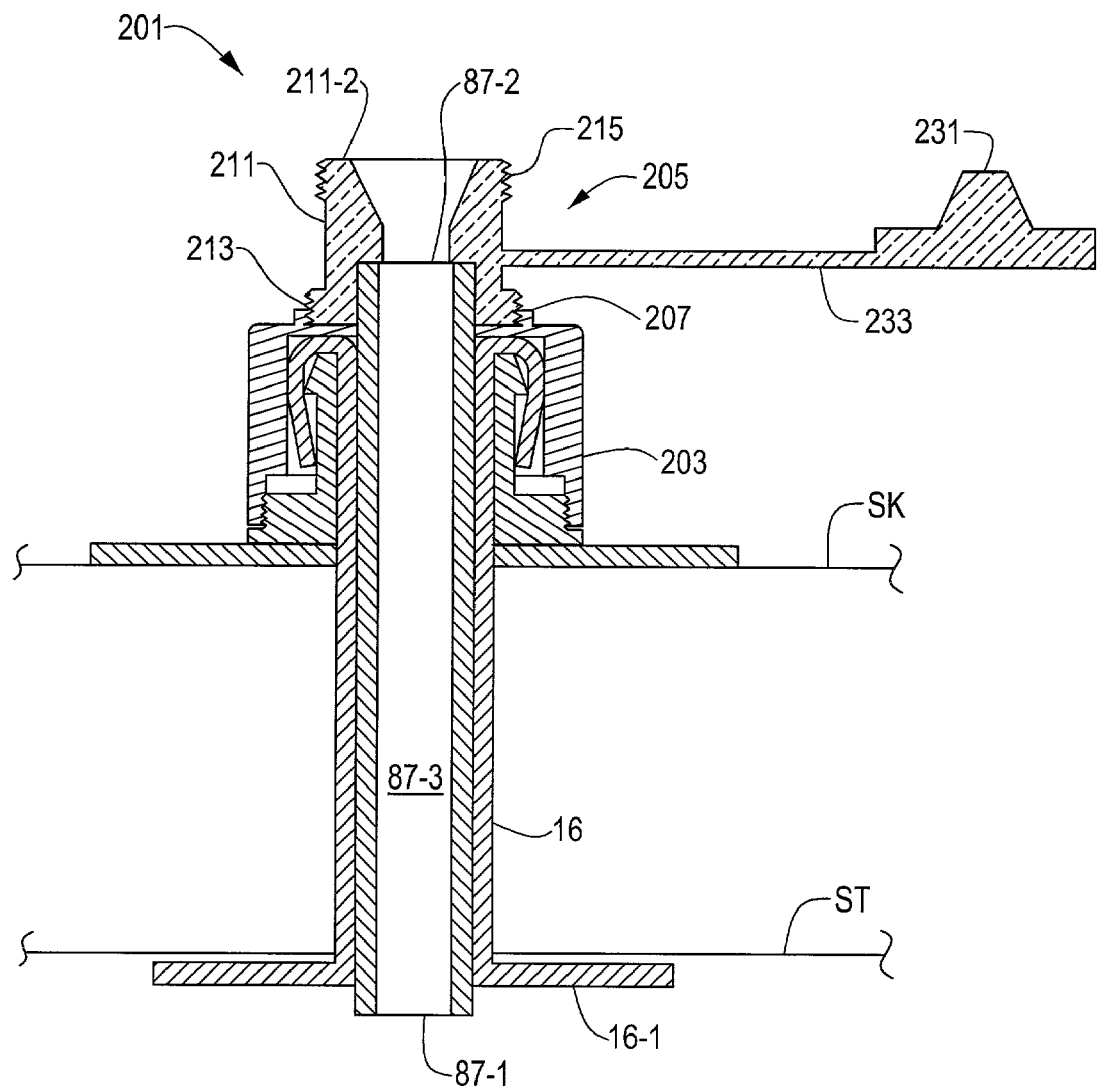
FIG. 18 is a section view of a second embodiment of a low profile medical catheter assembly constructed according to the teachings of the present invention, the low profile medical catheter assembly being shown implanted in a patient.
Figure 19:
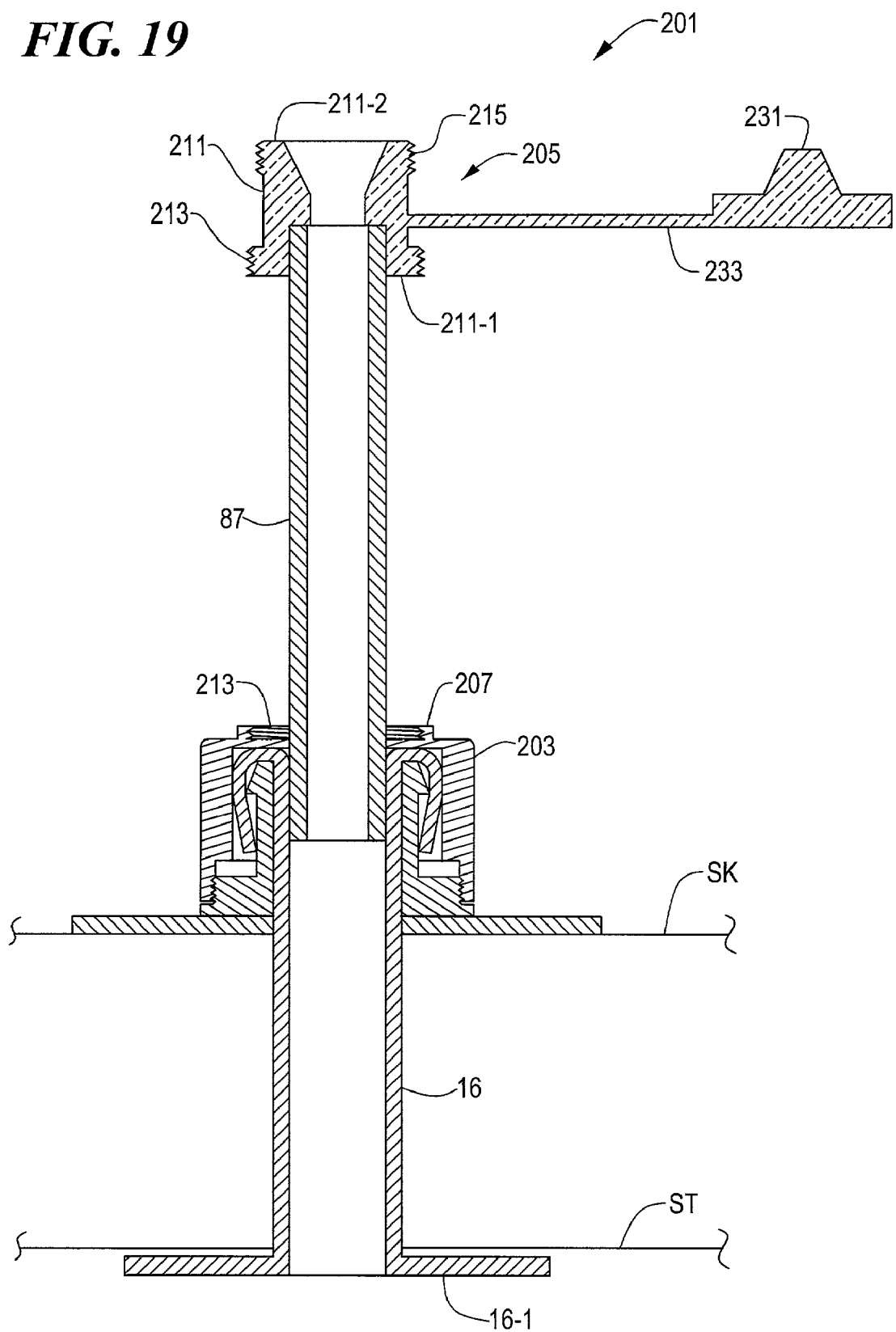
FIG. 19 is a section view of the low profile medical catheter assembly of FIG. 18, with the inner sleeve assembly partially removed from the gastrostomy feeding tube.

Referring now to FIGS. 18 and 19, there are shown section views of a second embodiment of a low profile medical catheter assembly constructed according to the teachings of the present invention, said low profile medical catheter assembly being represented generally by reference numeral 201.

Assembly 201 is similar in many respects to assembly 11, the principal differences between the two assemblies being that (i) assembly 201 does not include clamp 15, (ii) cap 17 is replaced with a cap 203, and (iii) inner sleeve assembly 18 is replaced with an inner sleeve assembly 205.

Cap 203, which is similar in many respects to cap 17, differs notably from cap 17 in that cap 203 further includes a collar 207 extending upwardly from top surface 71 and surrounding opening 81. A helical thread 209, whose purpose will become apparent below, is formed on the inside surface of collar 207.

Figure 20:
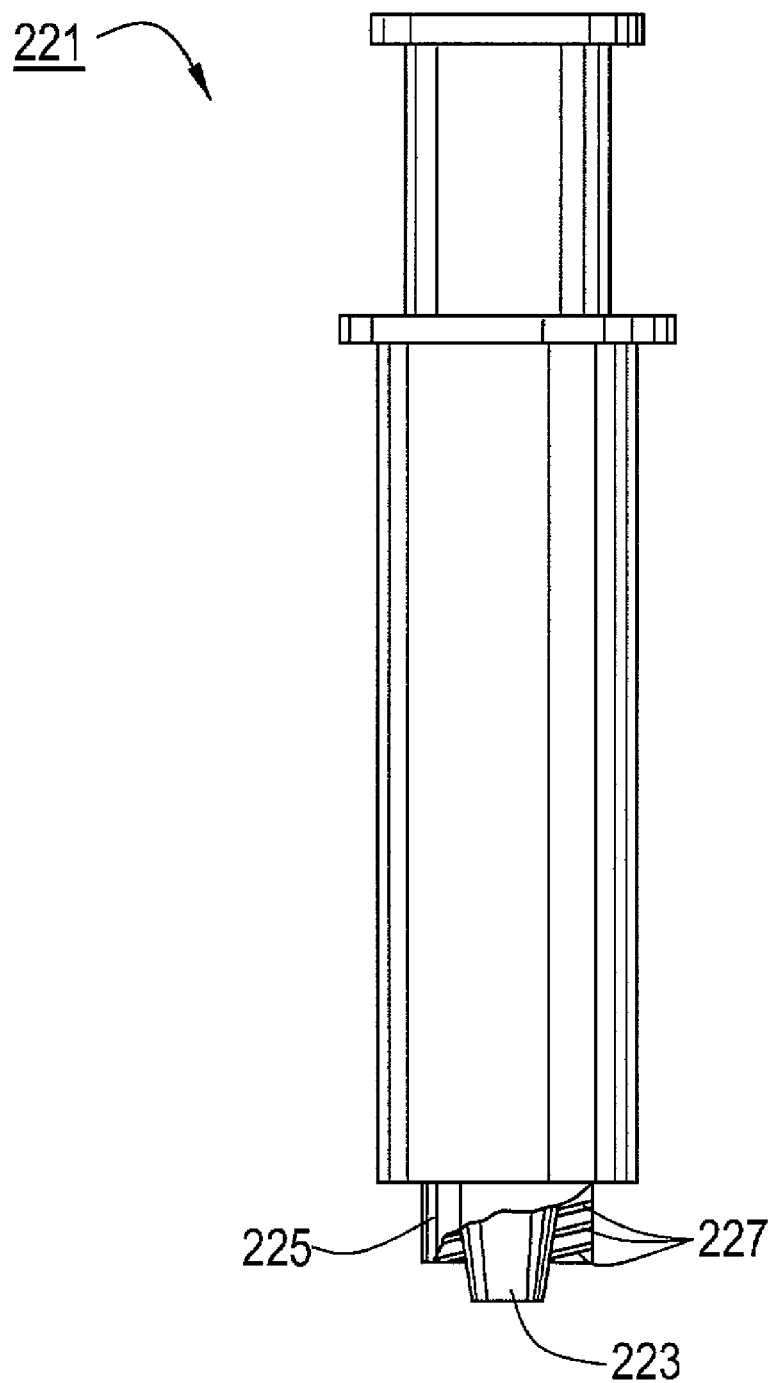
FIG. 20 is an enlarged front view, broken away in part, of a syringe adapted for use with the medical catheter assembly of FIG. 18.

Inner sleeve assembly 205, which is similar in certain respects to inner sleeve assembly 18, differs notably from assembly 18 in that fitting 89 of assembly 18 is replaced with a fitting 211. Fitting 211 differs from fitting 89 in that (i) an external helical thread 213, engageable with thread 209, is provided at the distal end 211-1 of fitting 211, (ii) an external helical thread 215 is provided at the proximal end 211-2 of fitting 211, and (iii) proximal end 211-2 is shaped to matingly receive a medical luer. (An exemplary syringe 221 having a medical luer 223 adapted for insertion into proximal end 211-2 and having a sleeve 225 with an internal thread 227 adapted to mate with thread 215 is shown in FIG. 20.)

Assembly 205 also comprises a plug 231 removably insertable into proximal end 211-2 of fitting 211 to seal fitting 211 shut between feedings (or drains). Plug 231 is connected to fitting 211 by a strap 233.

Assembly 201 is used in much the same way as assembly 11, the principal differences being (i) that inner sleeve assembly 205 is intended to remain in place at all times, except during repair or replacement and (ii) assembly 201 is designed for use with syringe 221, as opposed to tube T.

Although the particular catheter assemblies described herein have been low profile catheter assemblies, it should be understood that the present invention is not limited to low profile catheter assemblies and could be applied to high profile catheter assemblies.

The embodiments of the present invention described above are intended to be merely exemplary and those skilled in the art shall be able to make numerous variations and modifications to it without departing from the spirit of the present invention. For example, the thickness of the side wall of the inner sleeve could be increased so as to decrease the inner diameter of the sleeve and, accordingly, decrease the flow of materials therethrough. As another example, the inner sleeve could have more than one lumen to permit infusion while providing suction. As still another example, a space could be provided between the sleeve and the gastrostomy feeding tube to permit infusion through said space and suction through the lumen of the sleeve. As still yet another example, the distal end of the sleeve could be tapered to a smaller diameter such that any material suction through the distal hole will not clog the larger diameter proximal lumen. As a further example, the sleeve could have different proximal hub configurations and or closures. As still a further example, more than one sleeve could be used, with one sleeve being inserted into another sleeve. All such variations and modifications are intended to be within the scope of the present invention as defined in the appended claims.

What is claimed is:

1. A medical catheter assembly comprising:
   (a) a medical catheter, said medical catheter having a proximal end, a distal end and a longitudinal bore, said distal end being shaped to define an internal bolster;
   (b) an inner sleeve, said inner sleeve having a proximal end and a distal end, at least a portion of said inner sleeve being removably disposed within said longitudinal bore of said medical and
   (c) a body, said body having a base and a sleeve, said base having a transverse bore, said sleeve extending upwardly from said base and having a longitudinal bore, said longitudinal bore of said sleeve being aligned with said transverse bore of said base, said proximal end of said medical catheter being inserted up through said transverse bore of said base and said longitudinal bore of said sleeve and then inverted over the top of said sleeve.

2. The medical catheter assembly as claimed in claim 1 further comprising a fitting, said fitting having an open proximal end and an open distal end, said open distal end of said fitting being coupled to said proximal end of said inner sleeve in such a way as to permit materials to pass between said fitting and said inner sleeve.

3. The medical catheter assembly as claimed in claim 2 wherein said open proximal end of said fitting is adapted to receive a medical luer.

4. The medical catheter assembly as claimed in claim 3 wherein said open proximal end of said fitting is externally threaded to matingly engage an internally threaded sleeve surrounding a medical luer.

5. The medical catheter assembly as claimed in claim 2 further comprising a plug, said plug being removably insertable into said open proximal end of said fitting to seal shut said fitting.

6. The medical catheter assembly as claimed in claim 5 wherein said plug is connected to said fitting by a strap.

7. The medical catheter assembly as claimed in claim 2 wherein said open proximal end of said fitting is adapted to receive a tube.

8. The medical catheter assembly as claimed in claim 1 further comprising a cap mounted on said sleeve and over the inverted proximal end of said medical catheter for securing the inverted proximal end of the medical catheter to said sleeve.

9. The medical catheter assembly as claimed in claim 8 wherein said cap has an opening, said opening being aligned with said longitudinal bore of said sleeve.

10. The medical catheter assembly as claimed in claim 9 further comprising a plug removably insertable into said opening in said cap, said plug being connected to said cap by a strap.

11. The medical catheter assembly as claimed in claim 8 further comprising a fitting mounted on said cap, said fitting having an open proximal end and an open distal end, said open distal end of said fitting being coupled to said proximal end of said inner sleeve in such a way as to permit materials to pass between said fitting and said inner sleeve.

12. The medical catheter assembly as claimed in claim 11 wherein said cap further comprises a collar, said distal end of said fitting being screwed into said collar.

13. The medical catheter assembly as claimed in claim 8 wherein said cap has an internal thread, wherein said sleeve has an external thread and wherein said cap is removably screwed onto said sleeve by threaded engagement of said internal thread and said external thread.

14. The medical catheter assembly as claimed in claim 1 wherein said inner sleeve has an open proximal end, a closed distal end, a side port and a channel extending from said open proximal end to said side port.

15. The medical catheter assembly as claimed in claim 14 wherein said closed distal end is rounded.

16. The medical catheter assembly as claimed in claim 1 wherein the top of said sleeve is shaped to include an external barb over which said proximal end of said medical catheter is inverted.

17. The medical catheter assembly as claimed in claim 1 wherein said inner sleeve is sized to form a seal with the inside surface of said medical catheter.

18. The medical catheter assembly as claimed in claim 1 wherein said inner sleeve is sized so as not to form a seal with the inside surface of said medical catheter, said medical catheter assembly further comprising a ring, said ring being mounted around said inner sleeve and forming a seal with the inside surface of said medical catheter.

19. The medical catheter assembly as claimed in claim 1 wherein said inner sleeve is sized to extend at least the entire length of said longitudinal bore of said medical catheter.

20. The medical catheter assembly as claimed in claim 1 wherein said inner sleeve has an open proximal end, an open distal end and a longitudinal bore extending from said open proximal end to said open distal end.

21. The medical catheter assembly as claimed in claim 1 wherein said medical catheter is a gastrostomy feeding tube.

22. A medical catheter assembly comprising:
(a) a medical catheter, said medical catheter having a proximal end, a distal end and a longitudinal bore, said distal end being shared to define an internal bolster;
(b) an inner sleeve, said inner sleeve having a proximal end and a distal end, at least a portion of said inner sleeve being removably disposed within said longitudinal bore of said medical catheter;
(c) a body, said body having a base and a sleeve, said base having a transverse bore, said sleeve extending upwardly from said base and having a longitudinal bore, said longitudinal bore of said sleeve being aligned with said transverse bore of said base, said proximal end of said medical catheter being inserted up through said transverse bore of said base and said longitudinal bore of said sleeve and then inverted over the top of said sleeve, wherein said sleeve further comprises a transverse slot, said transverse slot intersecting said longitudinal bore; and
d) a clamp mounted on said base and movable within said transverse slot between a first position in which said clamp is adapted to transversely compress to closure the medical catheter when the inner sleeve is removed therefrom and a second position in which said clamp is not adapted to transversely compress the medical catheter.

23. The medical catheter assembly as claimed in claim 22 wherein said medical catheter assembly is a low profile PEG device.

24. The medical catheter assembly as claimed in claim 22 wherein said clamp is slidably mounted within said transverse slot and has a transverse opening, said transverse opening having a wide circular portion and a narrow slit portion, said narrow slit portion being aligned with said longitudinal bore of said sleeve in said first position, said wide circular portion being aligned with said longitudinal bore in said second position.

* * * * *